United States Patent
Steinbach et al.

(10) Patent No.: US 6,730,060 B1
(45) Date of Patent: May 4, 2004

(54) IMPLANTABLE DEVICE FOR ADMINISTERING A TREATMENT SOLUTION AND OPERATING DEVICE FOR A SYRINGE FOR FILLING THE DEVICE

(75) Inventors: Bernd Steinbach, Friedberg (DE); Walter Pieper, Florstadt (DE); Rüdiger Bernard, Oberthal (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/322,467

(22) Filed: May 28, 1999

(30) Foreign Application Priority Data

May 29, 1998 (DE) .......................................... 198 24 016

(51) Int. Cl.⁷ ...................... A61M 37/00; A61M 5/00; A61K 9/22
(52) U.S. Cl. ...................... 604/131; 604/891.1; 604/86; 604/247
(58) Field of Search .............................. 604/30, 93.01, 604/131, 132, 175, 247, 288.01–288.03, 500, 151, 502, 513, 236, 890.1, 891.1, 83–86; 128/DIG. 12

(56) References Cited

U.S. PATENT DOCUMENTS

| | | | |
|---|---|---|---|
| 4,175,563 A | * | 11/1979 | Arenberg et al. ............... 604/9 |
| 4,258,711 A | * | 3/1981 | Tucker et al. ........... 128/207.19 |
| 4,360,019 A | * | 11/1982 | Portner et al. ........... 128/213 R |
| 4,424,058 A | | 1/1984 | Parsons et al. |
| 4,496,343 A | | 1/1985 | Prosl et al. |
| 4,781,686 A | | 11/1988 | Erickson |
| 4,857,056 A | | 8/1989 | Talonn |
| 4,898,585 A | * | 2/1990 | Borsanyi et al. ............. 604/153 |
| 4,978,338 A | * | 12/1990 | Melsky et al. .......... 604/288.02 |
| 5,336,194 A | * | 8/1994 | Polaschegg et al. ......... 604/175 |
| 5,527,278 A | * | 6/1996 | Ensminger et al. ............ 604/93 |
| 5,575,770 A | * | 11/1996 | Melsky et al. ................. 604/93 |

FOREIGN PATENT DOCUMENTS

| | | |
|---|---|---|
| DE | 3342407 | 6/1985 |
| DE | 44 34 114 | 4/1995 |
| EP | 0 584 569 | 3/1994 |
| EP | 0 612 535 | 8/1994 |
| WO | WO 88 10129 | 12/1988 |
| WO | 96/31246 | 10/1996 |

* cited by examiner

Primary Examiner—Michael J. Hayes
(74) Attorney, Agent, or Firm—Kenyon & Kenyon

(57) ABSTRACT

An implantable device for administering a treatment solution has a first chamber for accommodating the active solution to be administered and a second chamber for accommodating a treatment solution bolus, each chamber having a port sealed with a septum. An infusion line leading to the infusion site is connected to the outlet of the first chamber. An inlet line branches off from the infusion line and is connected to the second chamber to accommodate the active solution bolus, and includes a flow device which releases the flow path to the infusion site only when the active solution bolus is supplied at a pressure above a predetermined minimum pressure. The occurrence of life-threatening situations due to sudden administration of a large quantity of active solution is prevented if the active solution is always supplied only at a pressure below the minimum pressure at which the flow path is released.

9 Claims, 2 Drawing Sheets

IMPLANTABLE DEVICE FOR ADMINISTERING A TREATMENT SOLUTION AND OPERATING DEVICE FOR A SYRINGE FOR FILLING THE DEVICE

FIELD OF THE INVENTION

The present invention relates to an implantable device for administering a treatment solution. In addition, the present invention concerns an operating device for a syringe for filling the device.

BACKGROUND INFORMATION

For uniform administration of a treatment solution over a lengthy treatment period, e.g. in the field of chemotherapy, there are known infusion pumps which are implanted in the patient's body.

U.S. Pat. No. 4,496,343 discloses an implantable infusion pump which has a medication reservoir that must be refilled at certain intervals. The disclosed infusion pump has a housing body which is divided by a membrane into two chambers. The first chamber contains the active treatment solution to be administered while the second chamber contains a propellant substance that is expandable under isobaric conditions. A housing port sealed by a puncturable septum is provided for transcutaneous refilling of the first chamber by an injection syringe.

To provide direct access to the catheter, the infusion pump has a third chamber connected by a channel to the first chamber for holding the active solution. The active solution flows through the channel from the first chamber into the third chamber and through a catheter out of the third chamber to the infusion site. The third chamber makes it possible to administer an additional quantity of active solution directly or to take samples. To administer the active solution or to take a sample using an injection syringe, a second housing port is provided and is sealed by a second puncturable septum.

Life-threatening situations can occur for a patient if the two septa are inadvertently confused. This is the situation when the quantity of active solution provided for the first chamber is injected partially or entirely into the third chamber for the bolus infusion or for sampling. In the case of morphine, for example, this can result in immediate apnea. It is relatively easy to confuse the two septa in practice because they are beneath the skin.

SUMMARY OF THE INVENTION

An object of the present invention is to increase the safety of implantable infusion pumps having an additional septum for a bolus infusion.

The present invention provides an implantable device for administering a treatment solution with a chamber (3) for holding the active solution to be administered, the chamber having a refilling port (6) which is sealed by a puncturable septum (5). A chamber (9) holds a treatment solution bolus, with the chamber having an inlet port (12) sealed by a puncturable septum (11). A connection (8) is provided for establishing a fluid connection between the chamber (3) for holding the active solution to be administered and an infusion site where the active solution is to be administered, as is a connection (13) for establishing a fluid connection between the chamber (9) for holding the active solution bolus and the infusion site. A conveyance mechanism (4) for conveying the active solution out of the chamber (3) for holding the active solution to be administered to the infusion site is also provided. The present invention is characterized in that the connection (13) for establishing a fluid connection between the chamber (9) for holding the active solution bolus and the infusion site include a device (14) which releases the flow path only when the active solution bolus is supplied to the chamber (9) at a pressure above a predetermined minimum pressure.

The present invention also provides an operating device for a syringe for filling the device with a holder (18) for attaching the barrel of the syringe, an operating element (21) for gripping the plunger of the syringe, and a drive device (22) for displacing the operating element so that the plunger is forced into the barrel of the syringe. The operating device is characterized in that the drive device (22) is designed so that the operating element (21) can be displaced out of a first position into a second position against a restoring force and can be locked in this position, and a releasing device (29) which releases the operating element is provided, the operating element being pushed back by the restoring force into the first position after being released.

The device according to the present invention for administering a treatment solution has a device which releases the flow path from the chamber for the bolus infusion to the site where the active solution is to be administered only when the active solution bolus is supplied to the chamber at a pressure above a predetermined minimum pressure.

Life-threatening situations due to sudden administration of a large quantity of active solution are prevented if the active solution for refilling the medication reservoir is always supplied only at a pressure below the minimum pressure. In case the septum of the medication reservoir is confused with the septum for the bolus infusion, the active solution cannot be administered because the fluid connection between the chamber for the bolus infusion and the infusion site will not be released.

The device clearing the flow path between the chamber for the bolus infusion and the infusion site only when a predetermined minimum pressure is exceeded not only prevents unintentional infusions but also prevents the active solution from reaching the chamber for the bolus infusion.

In a preferred embodiment, the device for clearing the flow path is a pressure control valve which is advantageously designed as a slitted disk, preferably made of silicone, with an opening pressure of 2 to 4 bar.

The device according to the present invention for administering a treatment solution is used together with an operating device which prevents the active solution from being supplied at a pressure above the predetermined minimum pressure when filling the medication reservoir. For refilling the medication reservoir, a traditional syringe is inserted into the operating device. The operating device has for this purpose a holder for attaching the barrel of the syringe, an operating device for gripping the plunger of the syringe and a drive device for displacing the operating element so that the plunger is forced into the barrel of the syringe.

For activation of the operating device, the operating element is prestressed against a defined restoring force, which causes the operating element to be pushed back to empty the syringe. The restoring force is such that the active solution is supplied from the syringe at a pressure which is below the minimum pressure of the device for clearing the flow path between the chamber for the bolus infusion and the infusion site. The pressure at which the active solution is supplied, however, is above the propellant pressure in the medication reservoir of the device for administering the active solution. A typical working range is between 1 and 1.5 bar.

The medication reservoir is filled when the tip of the syringe inserted into the operating device is beneath the septum of the chamber for holding the active solution when refilling the medication reservoir. However, if the tip of the needle is beneath the septum of the chamber for holding the active solution bolus, this effectively prevents an infusion administration error. Likewise, infusion is prevented if the tip of the needle is in one of the septa.

To administer a treatment solution bolus, a syringe for holding the active solution may be operated manually to build up a pressure above the predetermined minimum pressure.

BRIEF DESCRIPTION OF THE DRAWINGS

One embodiment of the device for administering a treatment solution as well as the operating device for a syringe for filling the device is explained in detail below with reference to the drawings, in which.

DETAILED DESCRIPTION

Figure 1:
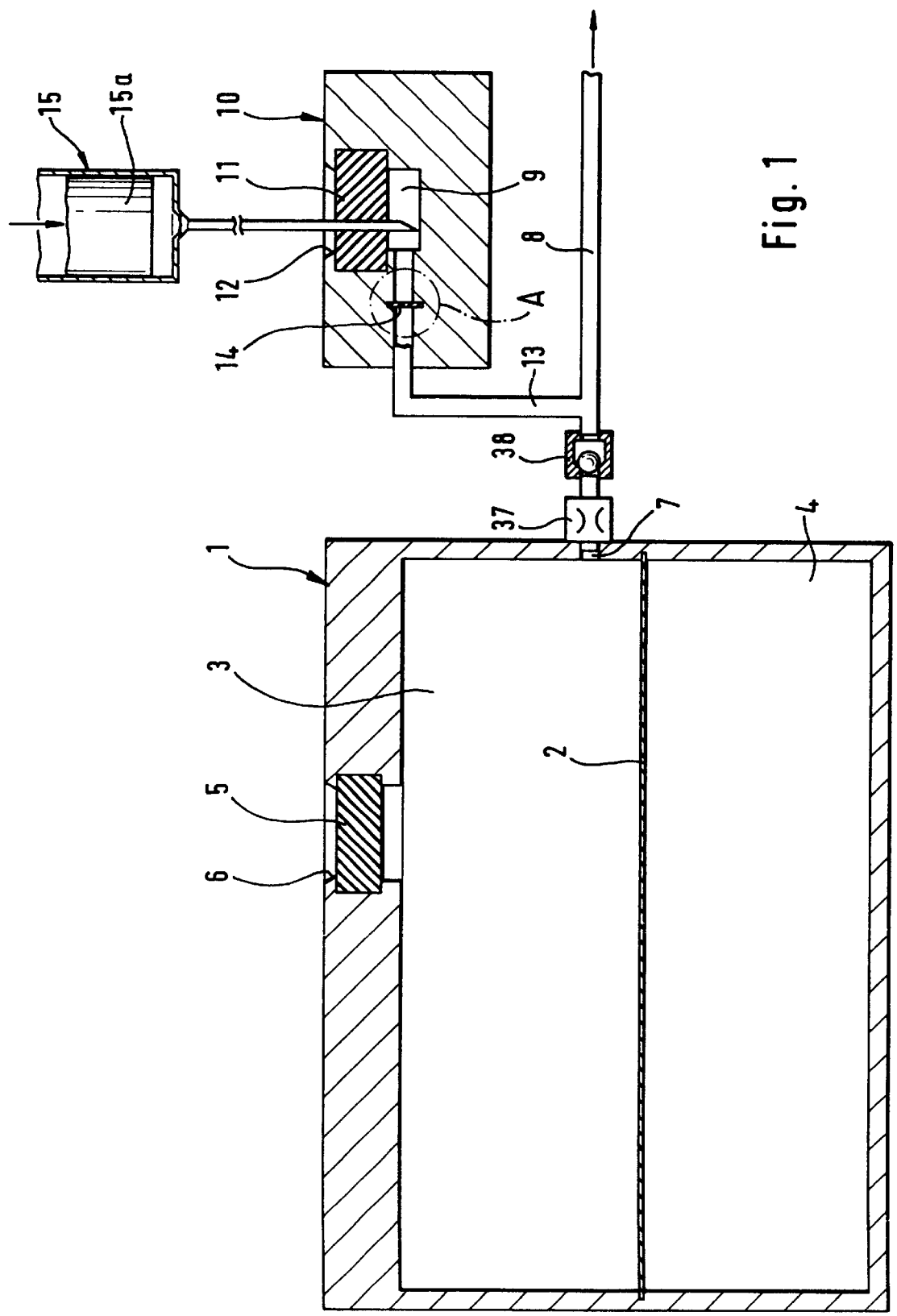
FIG. 1 shows an embodiment of the implantable device for administering a treatment solution in a schematic diagram.

The device for administering a treatment solution, in particular a medication, has an implantable housing body 1 which is divided by a flexible membrane 2 into a first chamber 3 and a second chamber 4.

The first chamber 3 holds the medication to be administered, while the second chamber 4 holds a propellant substance that is expandable under isobaric conditions.

The first chamber has an inlet port 6 which is closed by a puncturable septum so that the chamber can be filled with medication transcutaneously by an injection syringe. Furthermore, the first chamber 3 has an outlet 7 to which is connected an infusion line 8 leading to the infusion site. Since the propellant substance which is expandable under isobaric conditions in the second chamber is exerting a uniform pressure on flexible membrane 2, the medication flows out of the first chamber 3 through the infusion line 8 to the infusion site. A throttle 37 is arranged in the infusion line 8 for adjusting the flow rate.

To administer a medication bolus, a third chamber 9 is provided in a second housing body 10 which is also arranged beneath the skin of the patient. The third chamber 9 has an inlet port 12 which is closed by a second puncturable septum 11. Downstream from outlet 7, an inlet line 13 branches off from the infusion line 8 and is connected to the third chamber 9. A pressure control valve 14 is arranged in the inlet line 13, clearing the flow path from the third chamber 9 to the infusion site when the medication bolus is supplied at a pressure above a predetermined minimum pressure. The pressure at which valve 14 opens is preferably between 2.5 and 3.5 bar.

Figure 2:
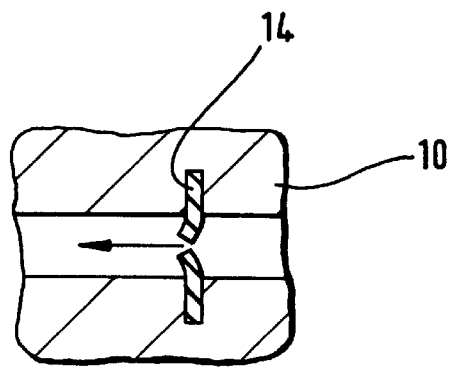
FIG. 2 shows a detail A from FIG. 1 on an enlarged scale.

FIG. 2 shows an enlarged diagram of pressure control valve 14. The pressure control valve is designed as a slitted silicone disk which is inserted into the second housing body 10.

For administration of a medication bolus, the third chamber 9 is filled with medication using, for example, a conventional injection syringe 15 whose needle is inserted through the second septum 11. By operating plunger 15a of injection syringe 15, a pressure above the predetermined minimum pressure at which pressure control valve 14 opens is built up. The medication bolus flows out of the third chamber 9 through the inlet line 13 and the infusion line 8 to the infusion site. Return flow of medication bolus into the third chamber 3 is prevented by a nonreturn valve 38 arranged in the infusion line 8 between outlet 7 of the first chamber and the inlet line 13.

Figure 3:
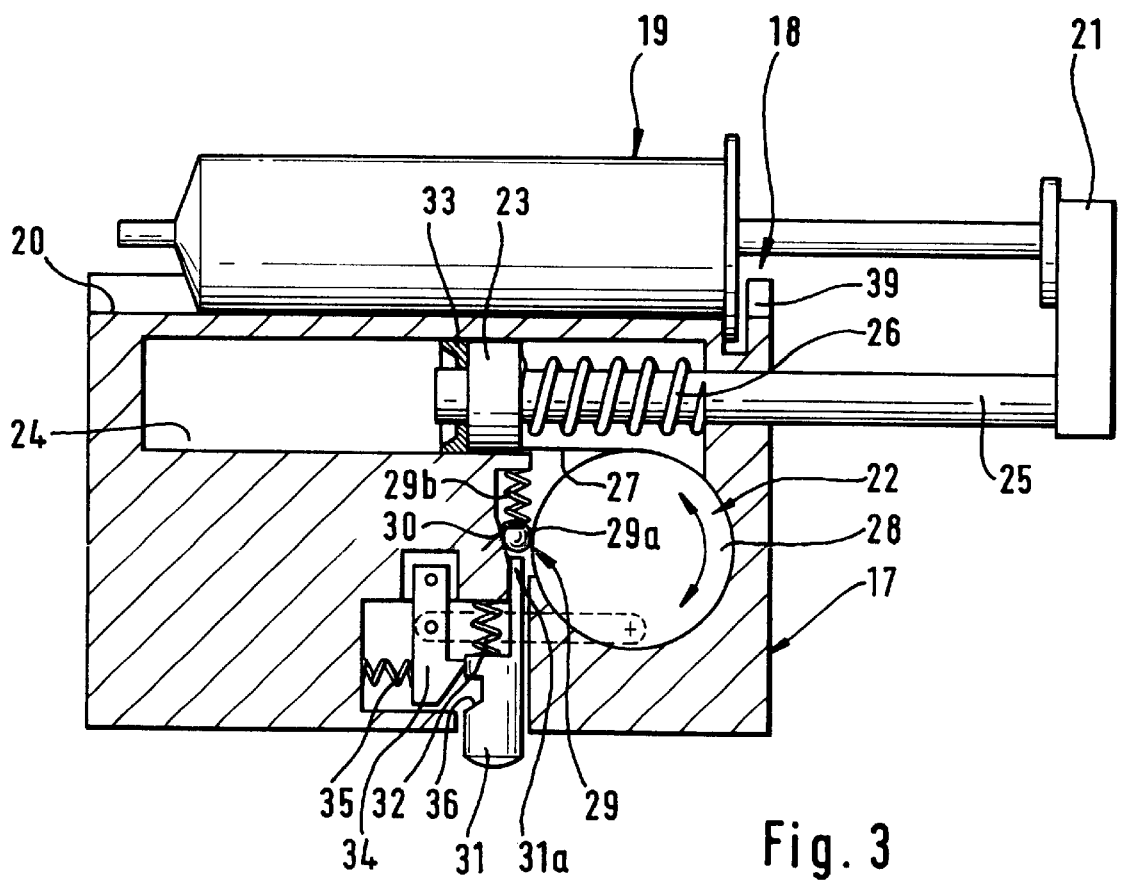
FIG. 3 shows a schematic diagram of one example of embodiment of the operating device for a syringe for filling the device for administering a treatment solution.

FIG. 3 shows an operating device for a syringe for refilling the first chamber 3 of the device for administering a medication.

The operating device has a housing body 17 with a holder 18 to which an injection syringe 19 is attached. Holder 18 includes a trough-shaped recess 20 for the barrel of the syringe 19 and a projecting shoulder 39 where the syringe is secured at the upper edge of the barrel.

In addition, the operating device has an operating element 21 which acts on the plunger of the syringe and is displaced by a drive device 22 in such a way that the plunger is forced into the barrel of the syringe.

Drive device 22 for operating element 21 includes a plunger 23 displaceably mounted in a barrel space 24 in housing body 17. A plunger rod 25 extending out of the housing body is attached to plunger 23, and operating element 21 for the plunger of syringe 19 is in turn attached to this plunger rod.

Before inserting syringe 19, the plunger is put under an initial stress against the restoring force of a compression spring 26 arranged in the barrel space 24 with a tension cable 27 attached to plunger 23 and wound onto a pulley 28 arranged in housing body 17. In the initially stressed position, pulley 28 is locked by a return lock 29. Return lock 29 has a ball 29a which is pressed by a compression spring 29b into a gap between pulley 28 and an inclined stop face 30, so that the pulley is secured and locked. Return lock 29 is released by a pushbutton 31 which is under spring tension with a compression spring 32 and is supported with a projecting shoulder 31a on ball 29a of return lock 29. When pushbutton 31 is pushed into housing body 17 against the force of spring 32, the projecting shoulder 31a pushes the ball 29a of return lock 29 back so that pulley 28 is released and operating element 21 is advanced into barrel space 24 under the restoring force of compression spring 26 to empty the syringe 19. In the position releasing the pulley, pushbutton 31 is held by a latch 34 which is under spring tension with a compression spring 35 and engages in a recess 36 in pushbutton 31.

So that operating element 21 will not suddenly snap back after return lock 29 is released, a damping element 33 which is supported on the wall of barrel space 24 is provided on the end face of plunger 23.

The restoring force of compression spring 26 arranged in barrel space 24 is such that the working pressure of syringe 19 is between 1 and 1.5 bar. Since this pressure is below the pressure at which the flow connection is established between the third chamber to hold the medication bolus and the infusion site, this prevents the possibility that a treatment solution intended for refilling the medication chamber might reach the patient directly.

What claimed is:

1. An implantable device for administering a treatment solution comprising:
    a first housing body including:
        a first chamber having a refilling port sealed by a first puncturable septum; and a conveyance mechanism for conveying the solution out of the first chamber to an infusion site;

a second housing body separately spaced from the first housing body and including a second chamber having an inlet port sealed by a second puncturable septum;

a first fluid connection for connecting the first chamber to the infusion site; and a second fluid connection for connecting the second chamber to the infusion site, the second fluid connection including a pressure control valve for preventing flow of the solution from the second chamber to the infusion site when the solution is supplied to the second chamber at a pressure below a predetermined minimum pressure, wherein the pressure control valve opens only when the solution is supplied to the second chamber at a pressure above the predetermined minimum pressure.

2. The device according to claim 1 wherein the first fluid connection includes an infusion line connected to the first chamber, the second fluid connection includes an inlet line connected to the second chamber and the infusion line, and the pressure control valve is arranged in the inlet line.

3. The device according to claim 2 wherein the pressure control valve includes a slitted disk.

4. The device according to claim 3 wherein the slitted disk includes silicone.

5. The device according to claim 1 wherein the predetermined minimum pressure is between 2 and 4 bar.

6. The device according to claim 5 wherein the predetermined minimum pressure is between 2.5 and 3.5 bar.

7. A method of administering a treatment solution comprising the steps of:

supplying a refillable first chamber having a refilling port sealed by a first puncturable septum, wherein a first housing body includes the refillable first chamber and a conveyance mechanism for conveying the solution out of the refillable first chamber to an infusion site, a first fluid connection connecting the refillable first chamber to the infusion site;

supplying a second chamber through a second puncturable septum, wherein a second housing body separately spaced from the first housing body includes the second chamber a second fluid connection connecting the second chamber to the infusion site;

supplying the solution to the infusion site via the first fluid connection; and preventing flow of the solution from the second chamber to the infusion site when the solution is at a pressure below a predetermined minimum pressure, wherein a treatment solution bolus is supplied from the second chamber to the infusion site through the second fluid connection including a pressure control valve which opens only when the treatment solution bolus is supplied to the second chamber at a pressure above a predetermined minimum pressure.

8. The method according to claim 7 wherein the predetermined minimum pressure is between 2 and 4 bar.

9. The method according to claim 8 wherein the predetermined minimum pressure is between 2.5 and 3.5 bar.

* * * * *